(12) United States Patent
Webster et al.

(10) Patent No.: US 10,173,029 B2
(45) Date of Patent: Jan. 8, 2019

(54) DEFLECTION CONTROL CATHETERS, SUPPORT CATHETERS AND METHODS OF USE

(71) Applicant: Otira Medical, Minneapolis, MN (US)

(72) Inventors: Mark W. I. Webster, Auckland (NZ); Jason Galdonik, Minneapolis, MN (US)

(73) Assignee: Otira Medical, Minneapolis, MN (US)

( * ) Notice: Subject to any disclaimer, the term of this patent is extended or adjusted under 35 U.S.C. 154(b) by 588 days.

(21) Appl. No.: 14/254,952

(22) Filed: Apr. 17, 2014

(65) Prior Publication Data

US 2014/0228808 A1    Aug. 14, 2014

Related U.S. Application Data

(63) Continuation of application No. 11/698,248, filed on Jan. 25, 2007, now abandoned.

(60) Provisional application No. 60/762,304, filed on Jan. 26, 2006.

(51) Int. Cl.
  *A61M 25/00*  (2006.01)
  *A61M 25/10*  (2013.01)
  *A61M 25/01*  (2006.01)
  *A61F 2/95*  (2013.01)

(52) U.S. Cl.
  CPC ........... *A61M 25/0023* (2013.01); *A61F 2/95* (2013.01); *A61M 25/0041* (2013.01); *A61M 25/01* (2013.01); *A61M 25/104* (2013.01); *A61M 2025/0183* (2013.01)

(58) Field of Classification Search
  CPC .............. A61M 25/0041; A61M 25/01; A61M 25/0023; A61M 25/104; A61F 2/95
  See application file for complete search history.

(56) References Cited

U.S. PATENT DOCUMENTS 4,402,685 A * 9/1983 Buhler ................. A61L 29/049
                                                                525/931
4,694,838 A * 9/1987 Wijayarthna ......... A61M 5/007
                                                                600/435

(Continued)

FOREIGN PATENT DOCUMENTS

EP    0282143    9/1988
EP    0377453    7/1990

(Continued)

OTHER PUBLICATIONS

Ashikaga et al., "Difficult Stent Deliver: Use of an Aspiration Catheter as a "Sheath"", Catheterization and Cardiovascular Interventions, 71:909-912 (2008).

(Continued)

*Primary Examiner* — Bradley J Osinski
*Assistant Examiner* — Matthew A Engel
(74) *Attorney, Agent, or Firm* — Dicke, Billig & Czaja, PLLC

(57) ABSTRACT

A deflection and support catheter provided for improved manipulation of elongated medical devices used during percutaneous procedures in difficult to reach situations. In particular, the deflection and support catheters can facilitate placement of guidewires, guide catheters, and intervention devices such as angioplasty balloons and stent delivery devices.

12 Claims, 17 Drawing Sheets

(56) References Cited

U.S. PATENT DOCUMENTS

| | | | | |
|---|---|---|---|---|
| 4,769,005 | A | * | 9/1988 | Ginsburg ............ A61M 25/01 604/164.13 |
| 4,771,782 | A | | 9/1988 | Millar |
| 5,088,991 | A | * | 2/1992 | Weldon ................ A61L 29/06 604/264 |
| 5,195,962 | A | * | 3/1993 | Martin ................ A61M 25/001 604/43 |
| 5,263,932 | A | * | 11/1993 | Jang ................ A61M 25/0023 604/160 |
| 5,489,278 | A | * | 2/1996 | Abrahamson ....... A61M 25/007 600/435 |
| 5,609,574 | A | * | 3/1997 | Kaplan ................ A61B 8/12 604/103.02 |
| 5,626,600 | A | * | 5/1997 | Horzewski ........ A61M 25/0054 606/194 |
| 5,738,667 | A | * | 4/1998 | Solar ................ A61F 2/95 604/103.04 |
| 5,772,639 | A | * | 6/1998 | Lampropoulos .. A61M 25/0014 604/264 |
| 5,817,072 | A | * | 10/1998 | Lampropoulos .. A61M 25/0017 604/264 |
| 5,827,229 | A | * | 10/1998 | Auth ................ A61B 17/22 604/164.13 |
| 5,876,373 | A | | 3/1999 | Giba et al. |
| 5,944,712 | A | | 8/1999 | Frassica et al. |
| 5,947,925 | A | * | 9/1999 | Ashiya ............ A61M 25/0169 604/164.08 |
| 6,027,461 | A | * | 2/2000 | Walker ............ A61M 25/0009 600/585 |
| 6,036,682 | A | | 3/2000 | Lange et al. |
| 6,096,073 | A | | 8/2000 | Webster et al. |
| 6,132,824 | A | | 10/2000 | Hamlin |
| 6,179,828 | B1 | * | 1/2001 | Mottola ............ A61M 25/0075 604/256 |
| 6,217,527 | B1 | | 4/2001 | Selmon et al. |
| 6,231,563 | B1 | | 5/2001 | White et al. |
| 6,290,693 | B1 | | 9/2001 | Jung, Jr. et al. |
| 6,596,020 | B2 | | 7/2003 | Vardi et al. |
| 6,610,069 | B2 | | 8/2003 | Euteneuer et al. |
| 6,682,536 | B2 | | 1/2004 | Vardi et al. |
| 6,692,483 | B2 | | 2/2004 | Vardi et al. |
| 6,869,417 | B1 | * | 3/2005 | Walters ................ A61M 25/00 604/164.1 |
| 2002/0032432 | A1 | * | 3/2002 | Nash ...................... A61M 25/00 604/533 |
| 2005/0148950 | A1 | | 7/2005 | Windheuser et al. |
| 2005/0267408 | A1 | | 12/2005 | Grandt et al. |
| 2005/0267442 | A1 | | 12/2005 | von Oepen |
| 2006/0142703 | A1 | | 6/2006 | Carter et al. |
| 2006/0210605 | A1 | | 9/2006 | Chang et al. |
| 2007/0060911 | A1 | * | 3/2007 | Webster ................ A61B 17/22 604/528 |
| 2007/0208302 | A1 | * | 9/2007 | Webster ............ A61M 25/0041 604/103.04 |

FOREIGN PATENT DOCUMENTS

| | | |
|---|---|---|
| EP | 1400208 | 3/2004 |
| WO | WO9836709 | 8/1998 |
| WO | WO9934749 | 7/1999 |
| WO | WO0012166 | 3/2000 |
| WO | WO2005030308 | 4/2005 |

OTHER PUBLICATIONS

International Search Report (PCT/US07/02149) dated Sep. 19, 2008.

Japanese Office Action for co-pending Japanese Patent Application No. 2008-552430 dated Jan. 2012 (6 pages).

Skyway Support Catheters brochure, Wire Support and Exchange for complex interventions by Vascular Solutions (2008).

Supplementary Partial European Search Report (PCT/US2007/002149) dated Jul. 1, 2010.

Takeshita et al., "Percutaneous coronary intervention using a novel 4-French coronary accessor", http://www3.interscience.wiley.com/cgi-bin/fulltext/119818183/main.html,ftx_abs (Jun. 10, 2008).

* cited by examiner

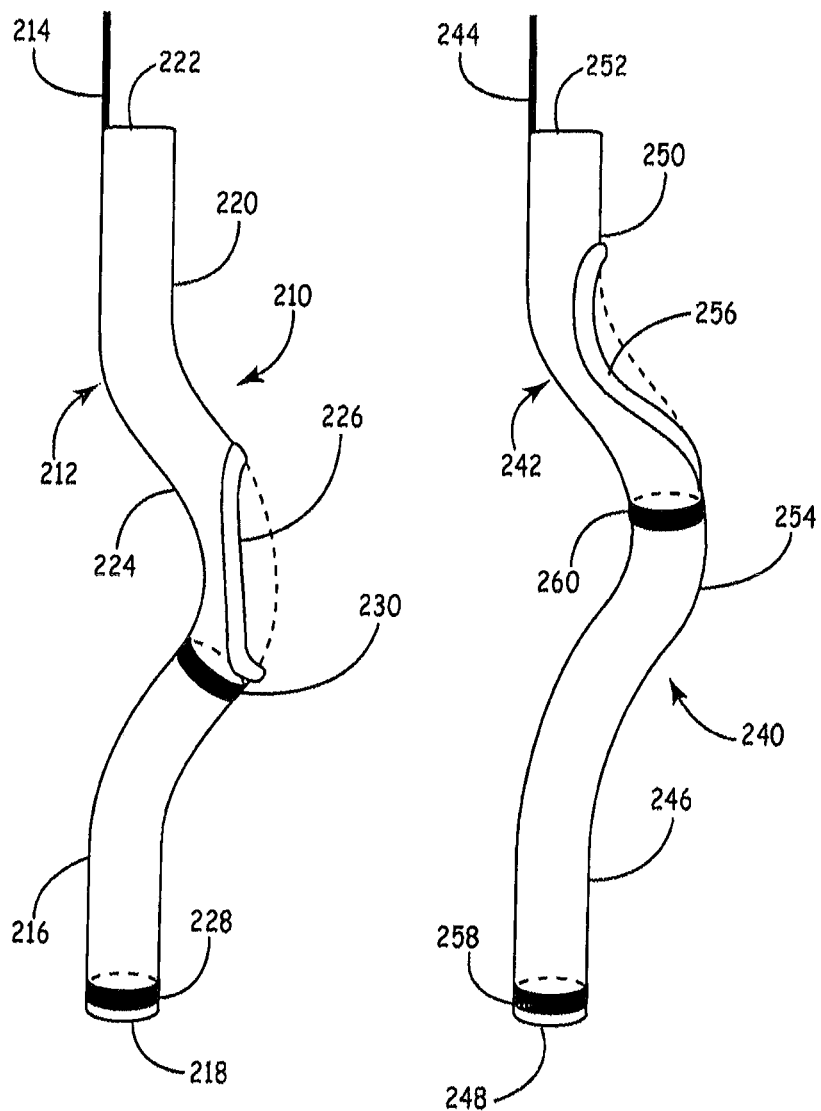

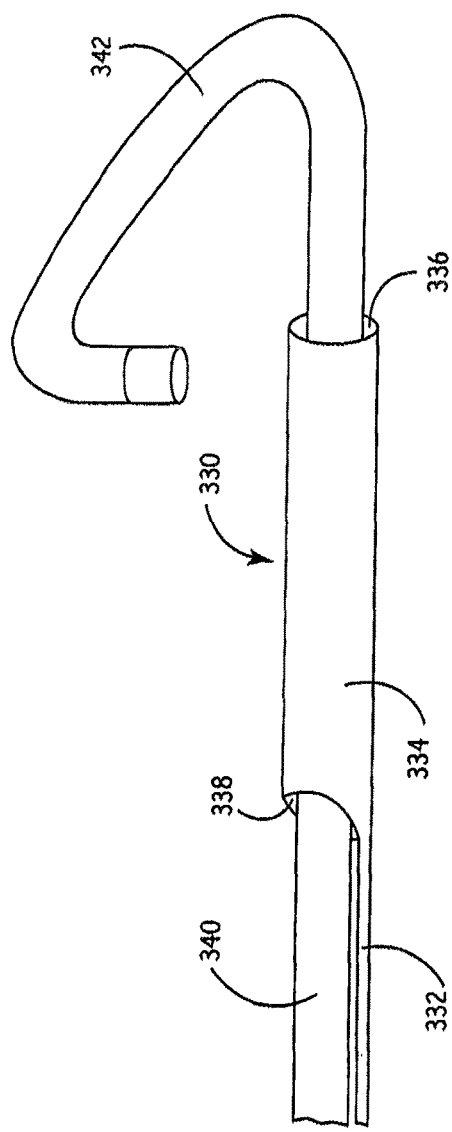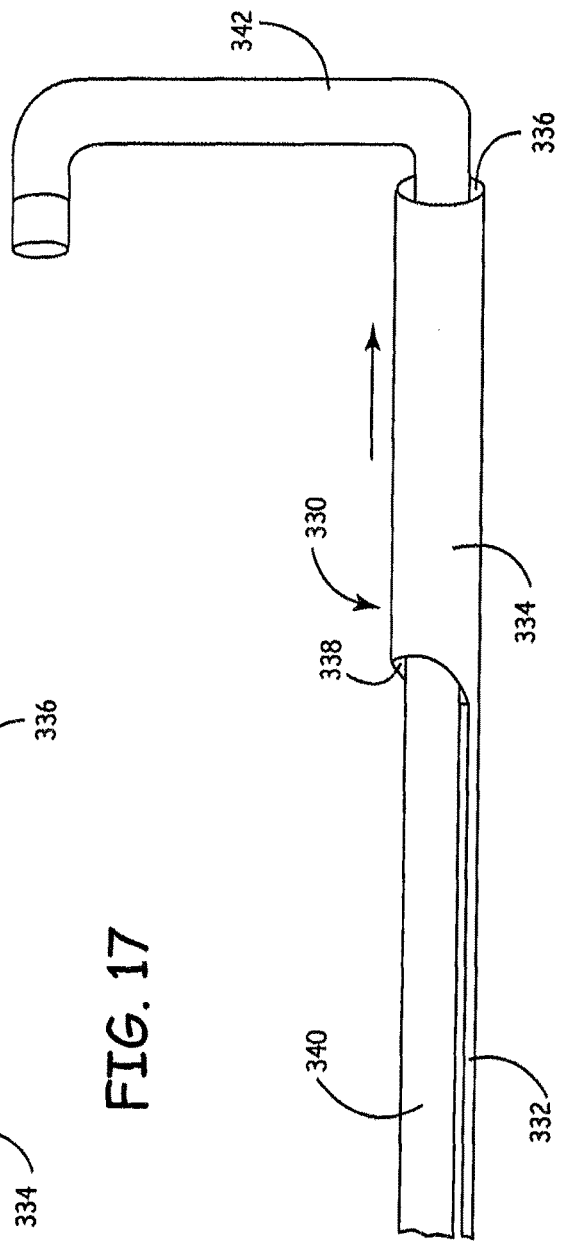
FIG. 17
FIG. 18

DEFLECTION CONTROL CATHETERS, SUPPORT CATHETERS AND METHODS OF USE

CROSS-REFERENCE TO RELATED APPLICATION(S)

This application is a continuation of U.S. patent application Ser. No. 11/698,248, filed on Jan. 25, 2007 and entitled "Deflection Control Catheters, Support Catheters and Methods of Use," which claims priority to U.S. Patent Application 60/762,304, filed on Jan. 26, 2006 and entitled "Deflection Control Catheter and Related Method of Use," both of which are hereby incorporated herein by reference in their entireties.

FIELD OF THE INVENTION

The invention relates to catheters to facilitate the delivery of guidewires, guide catheters or other interventional devices within a branched vascular network. The invention further relates to methods for the delivery of guidewires, guide catheters or other interventional devices along branched vessels in a body.

BACKGROUND OF THE INVENTION

Percutaneous vascular procedures are performed in many vessels in the body, including, for example, the coronary arteries, saphenous vein grafts, carotid arteries, cerebral vessels, and peripheral vessels. These procedures generally require the physician to gain access to the target vessel with a guiding catheter or sheath and track a guidewire into the vessel past a lesion or other location for the performance of a treatment procedure. One common complication of percutaneous procedures is the inability to gain access to a vessel and thus to properly position the interventional devices past the target position. Anatomical variations, such as lesion size and morphology, vessel tortuosity, and vessel take off angle contribute to these complications. Additional factors, such as poor guide support, can further lead to crossing issues. These complications can be compounded when the patient has previously received a stent, when the target lesion is located at a bifurcation, or when the patient has a chronic total occlusion where the vessel is completely or almost completely blocked.

BRIEF SUMMARY OF THE INVENTION

In a first aspect, the invention pertains to a catheter comprising a proximal segment and a rapid exchange segment connected at or near the distal end of the proximal segment. The rapid exchange segment comprises a tubular element with a lumen having a slit structure and sufficient rigidity to track over a cylindrical object within the lumen by pushing from the proximal end of the proximal segment.

In a further aspect, the invention pertains to a medical delivery tool for elongated medical devices. The tool comprises a flexible rod and a tubular element operably connected to the rod. The tubular element has a distal opening, a proximal opening and an open lumen connecting the distal opening and the proximal opening such that the tubular element forms a rapid exchange element to fit over an elongated medical device. In some embodiments, the tubular element has a side port.

In another aspect, the invention pertains to a method for the delivery of an elongated medical device into a vessel within a vascular network. The method comprises loading a rapid exchange segment of a delivery tool onto the elongated medical device and using the delivery tool to provide support for the placement of the elongated medical device into the vessel. The rapid exchange segment generally comprises a slit that provides for the loading of the rapid exchange segment.

In other aspects, the invention pertains to a method for the delivery of a guidewire into a vessel within a vascular network. The method comprises extending a curve tip of the guidewire through a side port of a deflection catheter into the vessel in which the side port is positioned at the opening into the vessel.

Moreover, the invention pertains to a catheter comprising a proximal section, and a rapid exchange segment operably connected to the proximal section. The rapid exchange segment comprises a tubular element having a guide lumen, a tip, a distal guide port and a side guide port, and the tubular element has a curve in the tip.

Furthermore, the invention pertains to a guidewire delivery system comprising a guidewire having a curved tip and a deflection catheter comprising a proximal section and a rapid exchange segment operably connected to the proximal section. The rapid exchange segment comprising a tubular element comprising a guide lumen, a distal guide port at the distal end of the guide lumen and a proximal guide port.

BRIEF DESCRIPTION OF THE DRAWINGS

FIG. 11 is a side view of a deflection and support catheter with a curved tip and a side port along a curved portion.

FIG. 12 is a side view of an alternative embodiment of a deflection and support catheter with a curved tip and a side port along a curved portion.

FIG. 17 is a fragmentary side perspective view of a rapid exchange deflection and support catheter riding over a medical device with a highly bent tip.

FIG. 18 is a fragmentary side perspective view of the catheter of FIG. 17 deflecting the medical device to a straighter orientation for placement into a branch vessel.

DETAILED DESCRIPTION

Figure 1:
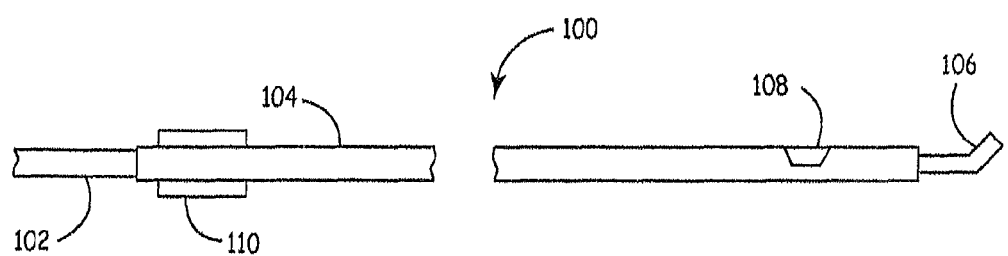
FIG. 1 is a fragmentary side view of a medical instrument delivery system with a deflection/support catheter and an elongated medical device.

A deflection and support catheter as described herein provides assistance to direct an elongate member within a blood vessel during a percutaneous procedure into a difficult to reach branch vessel. The deflection and support catheter can provide both direction and support for entering into a difficult branch vessel to navigate. In some embodiments, the deflection and support catheter has a side port at a stiffened section to provide support while the elongate member is directed through the side port into a difficult to reach vessel. In appropriate embodiments, once the side port is properly positioned, the curved tip of the elongate member, such as a guidewire, facilitates the entry of the elongate member out from the side port into the difficult to reach vessel. With the support from a deflection and support catheter, the physician can manipulate a guidewire past difficult to reach positions in the branch vessel, such as past thrombus accumulated at or near the vessel opening. Once the guidewire is in position, the deflection and support catheter can be removed, and the guidewire can be used to guide treatment structures, such as angioplasty balloons and stents into the branch vessel. In other embodiments, support and increased manipulation can be provided for the guiding catheter or sheath with a deflection and support catheter that similarly provides support for the distal end of a guide catheter. Interaction between the curve of the guiding catheter and the deflection and support catheter can aid in steering and push. In this embodiment, the support catheter generally has a rapid exchange segment that can clip over a guide catheter. In a further embodiment, the deflection and support catheter can be configured to ride over the shaft of an interventional device such as a balloon or stent system. The deflection and support catheter can provide increased support to the distal segment of the interventional device that extends out the distal end of the guiding catheter or sheath.

The deflection catheters described herein are generally useful for the placement of guidewires or catheters in difficult to reach vessels within the body of a patient, generally a human, although the device can be used in other mammals. Similarly, the deflection and support catheters are useful to facilitate the deployment of guide catheters. Once the guidewire/guide catheter/interventional device is placed at the desired location, the deflection/support catheter is generally removed. In some embodiments, the treatment structure or medical instrument is placed at or past a lesion, which can be thrombus within in the vessel.

The deflection and support catheter can have an over the wire or rapid exchange configuration. In a rapid exchange configuration, the elongate member extends within only a portion of the catheter. The catheter generally has a guide port at its distal tip. For rapid exchange embodiments, a rapid exchange guide port is located to define a guide lumen extending from the rapid exchange guide port to the distal port. The side port is located at an appropriate position between the rapid exchange port and the distal port. For embodiments that support and deflect other interventional devices down difficult vasculature, the catheter has an overall length to reach the target vessel from an appropriate insertion point into the patient. For embodiments that support and deflect other interventional devices, the catheter has an overall length to reach the distal end of the interventional device.

In the rapid exchange configuration, the proximal portion of the catheter extending in a proximal direction from the rapid exchange port can be solid or tubular while providing a desired degree of strength and flexibility since this section of catheter only provides a mechanical function. In particular, the proximal portion of the catheter can have a rod structure, a tubular structure or other similar elongated form, with a flat, circular or other appropriate cross section shape. The proximal section is used only advance, withdraw and steer the rapid exchange segment within the vessel from a section that is exterior to the patient. Thus, this proximal segment should be stiff enough to push the rapid exchange segment, and it should transmit torque for steering. However, this proximal segment generally does not need an open lumen or an outer surface suitable for the passage of instruments. Also, it is advantageous for this segment to be of low profile.

In some embodiments, the deflection and support catheter has a side port that is configured to facilitate the guiding of an elongate member, such as a guidewire, out from the side port. The side-guide port should be configured to allow for relatively easy passage of a tip, generally a curved, tip of a guidewire to exit the side port. For some embodiments, the widest diameter across the port opening in some embodiments is at least 1.5 times the size of the guidewire diameter and in other embodiments at least twice the size of the guidewire diameter. The guide catheter can then support the movement of the guidewire into a branch vessel even past an occlusion while not making the task of the health care provider excessively difficult. Generally, the side guide port does not have a tubular projection so that there is no extraneous structure to snag while moving the structure within a vessel. However, the side port can be reinforced. In general, there is no projection of a millimeter or greater from the side port relative to the surface of the catheter.

In some embodiments, the deflection and support catheter has curves at its tip for either an over the wire or rapid exchange configuration. The curve can assist with placement of the side port adjacent to an opening into a side branch vessel. The catheter can have one or more curves along the length. It can be advantageous to have two, three or more curves.

To provide additional support and to reduce or eliminate kinking, it can be desirous to have a stiffened section at or near the side port. Thus, the section surrounding the side port can be stiffer than proximal and distal segments. Alternatively or additionally, the section around the port can be stiff relative to other sections of the catheter. The stiffness can be provided by coating or embedding a wire or reinforcement at the appropriate section and/or by using a different material welded or otherwise connected to adjacent material. Furthermore, the side port section can be constructed with one or more radiopaque bands that aid in visualization and also provide increased stiffness. In some embodiments, the stiffened section has a stiff measured with a Durometer value of at least about 60 D.

In alternative embodiments, the deflection and support catheter has a bent tip with appropriate stiffness so that a guidewire or catheter extending outward from the tip can hold the tip straight if extending sufficient from the tip, or the tip can bend if the guidewire/catheter is extending only a short distance from the tip. This embodiment provides an alternative to embodiments with a side port.

To use the deflection and support catheter for delivery of a guidewire into a branch vessel, the guidewire is directed into the main vessel past the branch point. The deflection catheter can be delivered over the guidewire while the guidewire is being delivered or after the guidewire is in place. Then, the deflection catheter is positioned with the side port adjacent the opening into the branch vessel. Placement can be facilitated using radiopaque markers on the deflection catheter or through visualization of radiopaque material forming at least along a portion of the deflection catheter, along with visualization dye in the vessel if desired. Once the deflection catheter is in place, the guidewire can be retracted so that its tip can exit through the side port. With the support of the deflection catheter the guidewire generally can be positioned past a lesion at or near the opening of the branch vessel. Similarly, the support of the deflection catheter can be used to reach into sharp bending branch vessels that are otherwise difficult or impossible to reach. Once the guidewire is in place, the deflection catheter can be removed. Thus, the deflection catheter provides for the performance of procedures that would not be otherwise possible.

In an alternative embodiment, the support catheter is used to support another interventional device such as a balloon or stent deploying instrument. This embodiment is referred to as a support catheter. The support catheter generally has a rapid exchange configuration. The tubular element of the support catheter has an inner lumen sufficiently large for the passage of a guide catheter of a selected diameter. A proximal section extends proximally from the rapid exchange segment. This proximal section should have enough stiffness to advance and withdraw the support catheter onto and off from the guide catheter. The rapid exchange segment has a slit structure that provides for loading and unloading the rapid exchange segment onto and off from the guide catheter or interventional device since the guide catheter or other interventional device generally has handles and other structures attached to its proximal end that makes it difficult or impossible to advance the support catheter over the end of the guide catheter. A slit refers broadly to any structure that provide for opening of the generally cylindrical lumen to extend the rapid exchange segment around the guide catheter. For example, the slit can have overlapping portions, locking portions or the like, and some representative embodiments are described further below.

Support catheter can be placed over the guide catheter or other elongated interventional device for placement into a vessel. The support catheter can be inserted into the patient if the health care professional is having difficulty placing a guide catheter at a desired location. The support catheter can provide additional support at the distal end of the guide catheter to facilitate placement of the guide catheter. Once the guide catheter is in place, the support catheter can be removed.

The advantages of the deflection catheter and support catheter can be further elucidated from the specific embodiments described in the following.

Deflection/Support Catheter Structure

The deflection/support catheter has a distal port as well as a side port and/or a proximal rapid exchange port. In embodiments of particular interest, the catheter has a rapid exchange segment with a rapid exchange port with the rapid exchange segment designed to ride over a medical device during a percutaneous procedure. In some embodiments, the rapid exchange segment can have a slit to provide easier placement over the medical device for loading. In additional or alternative embodiments, the deflection and support catheter has a curved tip and/or a curved distal portion. A side port, if present, can be configured to provide exit of the tip of the elongated medical device directed with the deflection/support catheter. The deflection/support catheter can be formed from a radiopaque material and/or can have one or more radiopaque marker bands to facilitate proper positioning in a patient.

A medical device delivery system comprises an elongated medical device and a deflection and support catheter that is designed to ride over the elongated medical device in an over the wire or rapid exchange configuration. Referring to FIG. 1, medical device delivery system 100 comprises an elongated medical device 102 and a medical delivery tool 104, e.g., a deflection catheter/support catheter. The elongated medical device 102 can be a guidewire, guide catheter, balloon catheter, stent delivery catheter or other percutaneous medical instruments, such as those well known in the art. A shown in FIG. 1, elongated medical device 102 has a bent tip 106. Guidewires as used herein can have a solid structure or an internal structures such as a hollow lumen or a core wire or the like. As shown in FIG. 1, medical delivery tool 104 has an optional side port 108 and an optional handle 110.

Figure 2:
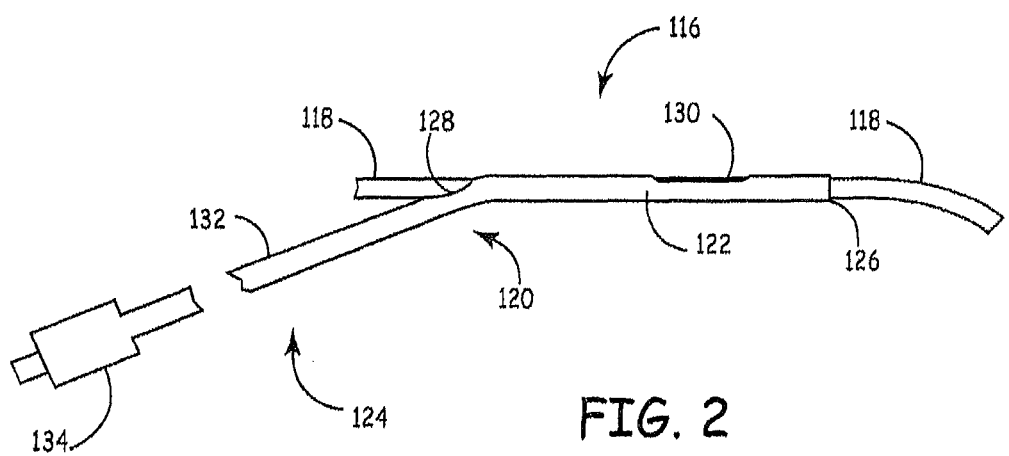
FIG. 2 is a fragmentary side view of a medical instrument delivery system with a rapid exchange deflection/support catheter and an elongated medical device.

Percutaneous tools with rapid exchange, or monorail, segments can be desirable due to their ease of loading. Referring to FIG. 2, Medical device delivery system 116 comprises an elongated medical device 118 and medical delivery tool 120. Elongated medical device 118 can be the same medical devices described with respect to elongated medical device 102. Medical delivery tool 120 has a rapid exchange segment 122 and a proximal extension 124. Rapid exchange segment 122 comprises a distal port 126 and a proximal port 128 that provide for an elongated medical device to pass within the rapid exchange segment. As shown in FIG. 2, rapid exchange segment 122 has an optional side port 130. Proximal extension 124 comprises an elongated element 132 and an optional handle 134. Elongated element 132 can comprise a tubular element, a solid rod or other elongated segment. A solid, flexible rod or wire is convenient as having a smaller diameter than other structures for selected mechanical properties, and a smaller diameter provides for less blockage of the vessels and passage through smaller guide catheters during use. During use elongated element 132 connects rapid exchange segment 122 within the patient with the exterior of the patient.

Figure 3:
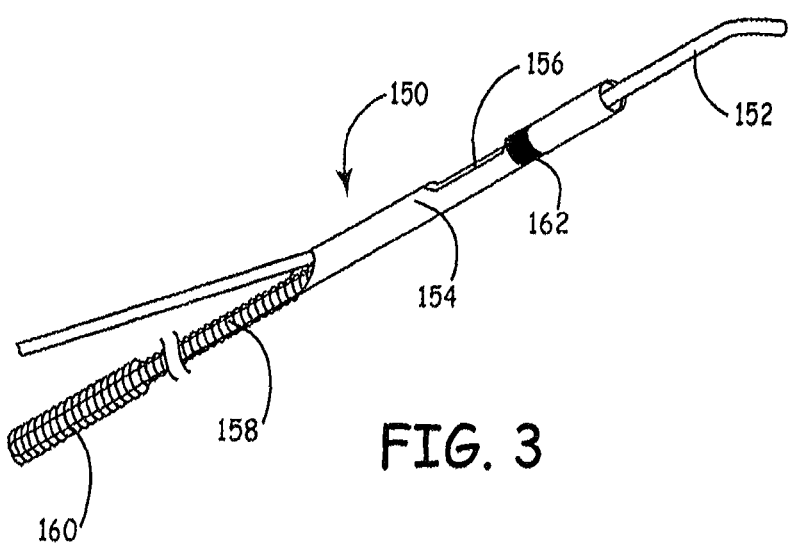
FIG. 3 is a fragmentary side view of an embodiment of a rapid exchange deflection and support catheter riding on a guide wire.

A particular embodiment of the medical delivery tool as a rapid exchange deflection/support catheter is shown in FIG. 3. Deflection and support catheter 150 can be used to deflect a guidewire 152 into a branch vessel in a patient. Catheter 150 comprises rapid exchange segment 154 with side port 156, rod 158 and handle 160. In this embodiment, rapid exchange segment 154 has a radiopaque marker band 162. For conventional guidewires, rapid exchange segment can have a 2 1/2 French diameter. As described further below, rapid exchange segment 154 can be formed from a polymer tube optionally with braided or wound metal wire embedded within the polymer.

Figure 4:
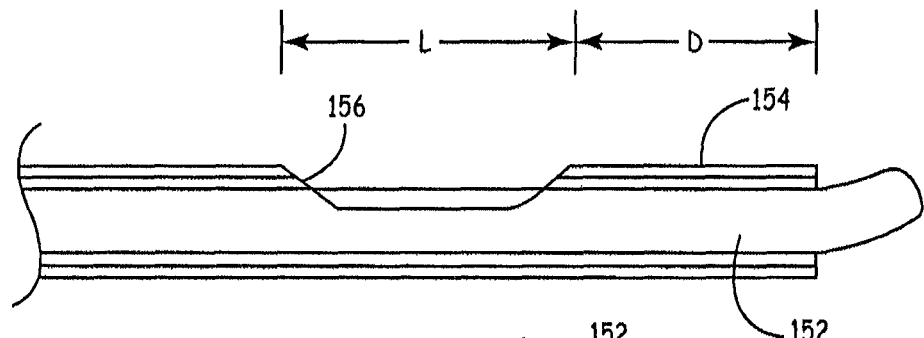
FIG. 4 is an expanded sectional view of the tip of the deflection and support catheter and guidewire of FIG. 4 with the section taken through the center of the catheter and guidewire.
Figure 5:
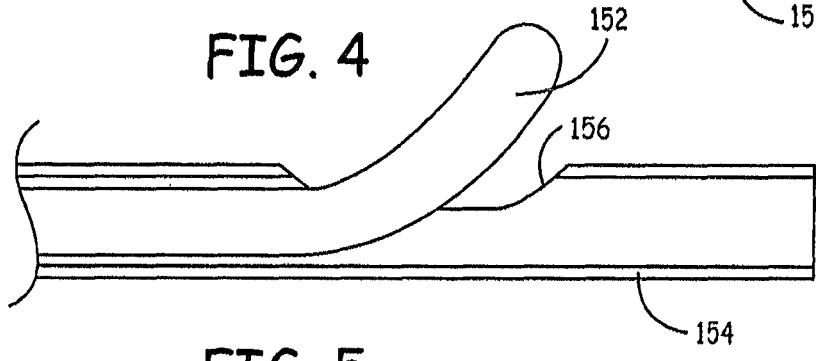
FIG. 5 is an expanded sectional view of the tip of the deflection catheter as shown in FIG. 4 with the tip of the guidewire extending from a side port of the catheter.

An expanded, fragmentary sectional view of rapid exchange segment 154 is shown in FIG. 4. Side port 156 should have a size and shape to facilitate exit of the tip of guidewire 152 out through side port 156. Thus, in some embodiments, the opening of side port 156 has a length along the longitudinal direction of the segment of at least about twice the diameter of guidewire 152, and at least a portion of rapid exchange segment has a stiffness corresponding with a durometer value of 60 D to support guidewire 152 as it is pushed through side port 156 possibly into a significantly blocked branch vessel. As shown in the particular embodiment of FIG. 4, the side port or window has a longitudinal dimension, L, of about 8 mm and a distal extension, D, of about 10 mm, although other dimensions are suitable as desired.

Figure 8:
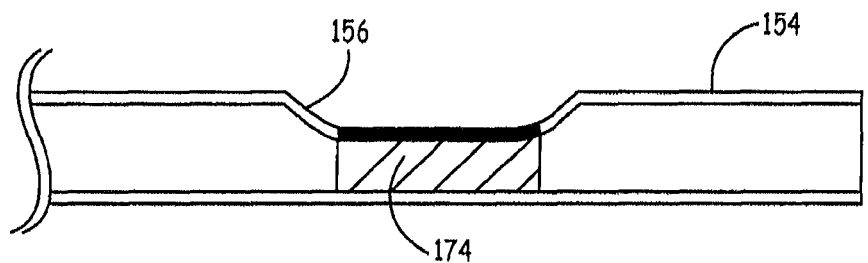
FIG. 8 is a fragmentary side view of an embodiment of a tip of a deflection and support catheter having a radiopaque marker below a side port.
Figure 6:
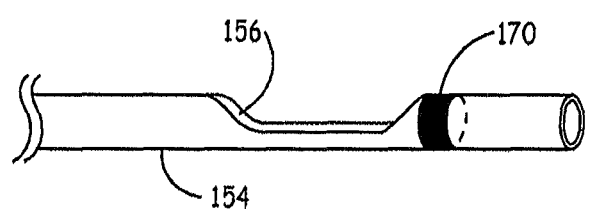
FIG. 6 is a fragmentary perspective view of an embodiment of a tip of a deflection and support catheter having a radiopaque marker band distal to a side port.
Figure 7:
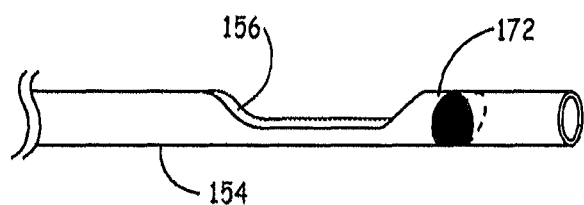
FIG. 7 is a fragmentary perspective view of an embodiment of a tip of a deflection and support catheter having a non-circumferential radiopaque marker.

Referring to FIG. 6, rapid exchange segment 154 is shown with a single marker band 170 having a cylindrical configuration at the distal end of side port 156. Referring to FIG. 6, rapid exchange segment 154 has a non-cylindrical marker band 170 that does not extend around the entire circumference of the rapid exchange segment. The non-circumferential marker may make it easier to align side port 156 during use. Referring to FIG. 8, rapid exchange segment 154 has a marker section 174 placed below side port 156 to again facilitate alignment of side port 156. In alternative embodiments, a plurality of marker bands can be used and/or the rapid exchange segment can be formed from a radiopaque material.

Figure 9:
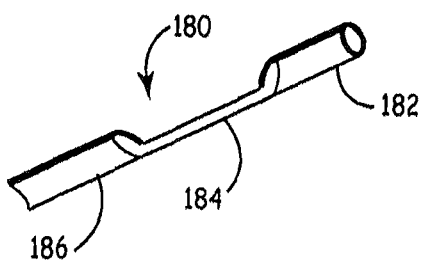
FIG. 9 is a fragmentary perspective view of a rapid exchange segment of a deflection and support catheter with a wire connecting a distal tubular portion and a proximal tubular portion.

An alternative embodiment of a rapid exchange segment for a deflection and support catheter is shown in FIG. 9. Rapid exchange segment 180 comprises a distal tubular element 182, a connecting rod or wire 184 and proximal tubular element 186, which connects to a rod or other elongated proximal element to extend out from the patient. Connecting rod 184 connects distal tubular element 182 with proximal tubular element 186. During placement of the deflection and support catheter, distal tubular element 182 and proximal tubular element 186 ride over the medical device. The gap between the proximal tubular element 186 and distal tubular element 182 can function as the side port for deflection of the guidewire or other medical device. In alternative embodiments, a plurality of wires can connect distal tubular element 182 and proximal tubular element 186 with the gap between the tubular elements still functioning as a side port.

Figure 10:
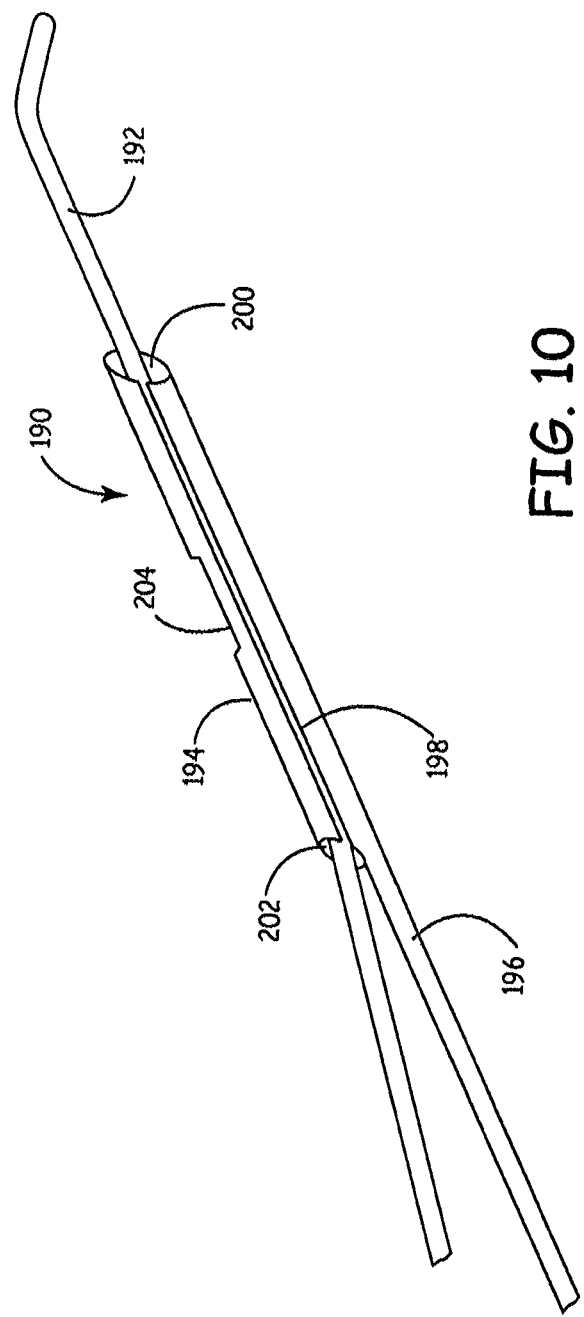
FIG. 10 is a fragmentary perspective view of a deflection and support catheter having a rapid exchange segment with a slit clipped onto an elongated medical device.

Referring to FIG. 10, deflection and support catheter 190 is shown clipped over guidewire or medical device 192. In this embodiment, deflection and support catheter 190 comprises a rapid exchange segment 194 and proximal rod 196. Rapid exchange segment 194 has a slit 198 extending along its length to facilitate clipping onto the guidewire 192. Rapid exchange segment 194 further has a distal port 200, a proximal port 202 and a side port 204. Slit 198 extends form distal port 200 to proximal port 202. Rapid exchange segment 194 has sufficient flexibility to open and close over guidewire 192 while having sufficient rigidity to remain over the guidewire as deflection catheter 190 is pushing into position. Slit 198 can be formed with overlapping sections, sections that meet, locking sections or other appropriate configurations that provide the functional features.

The deflection and support catheter can have curves that deflect the side port away from the axis of the distal and proximal ports. Two embodiments with curved rapid exchange segments are shown in FIGS. 11 and 12. Referring to FIG. 11, deflection and support catheter 210 comprises rapid exchange segment 212 and proximal rod 214. Rapid exchange segment 212 has a distal segment 216 with a distal port 218, proximal segment 220 with a proximal port 222, and a curved segment 224 between distal segment 212 and proximal segment 220. Side port 226 is located at the center of curved segment 224 where the curved segment in its natural shape is deflected furthest from the axis connecting distal port 218 with proximal port 222. In this embodiment, rapid exchange segment 212 has a first radiopaque marker band 228 near distal port 218 and a second radiopaque marker band 230 near the distal edge of side port 226. In some embodiments, the side port comprises a cut out of a portion of the tubular element in which the cut out has a length along the axis of the tubular element from about 1 to about 4 millimeters and a minimum circumference along the port of ⅓ of the average circumference around the tubular element away from the side port.

Referring to FIG. 12, deflection and support catheter 240 comprises rapid exchange segment 242 and proximal rod 244. Rapid exchange segment 242 has a distal segment 246 with a distal port 248, proximal segment 250 with a proximal port 252, and a curved segment 254. Side port 256 is located the outside proximal edge of curved segment 254 relative to the position of the curved segment in its natural shape that is deflected furthest from the axis connecting distal port 248 with proximal port 252. In this embodiment, rapid exchange segment 242 has a first radiopaque marker band 258 near distal port 248 and a second radiopaque marker band 260 near the distal edge of side port 256.

Figure 13:
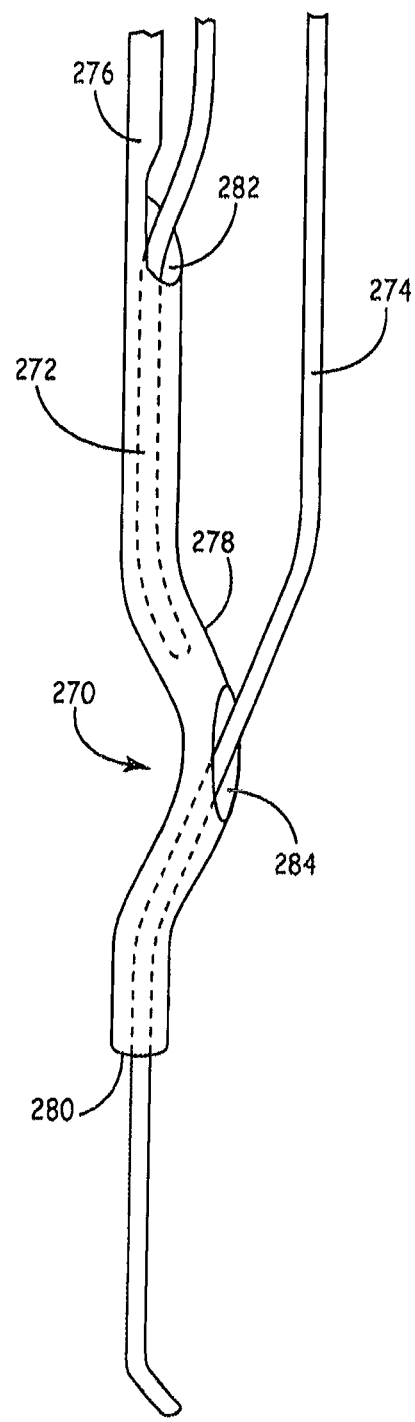
FIG. 13 is a side view of an embodiment of a deflection and support catheter used with two guidewires with hidden structure of the guidewires shown in phantom lines.

A two wire embodiment is depicted in FIG. 13. Referring to FIG. 13, deflection catheter 270 is interfaced with first guidewire 272 and second guidewire 274. Guidewires 272, 274 can be substituted for other appropriate elongated medical devices. Deflection and support catheter 270 comprises a proximal extension 276 and rapid exchange segment 278. Rapid exchange segment 278 comprises a distal port 280, a proximal port 282 and a side port 284. In this embodiment, rapid exchange segment 278 has a curve, and side port 284 is located at the maximum deflection of the curve, although other placements of the side port can be used as desired. Generally, side port 284 is large enough for the passage of both guidewires 272, 274. First guidewire 272 and deflection and support catheter 270 can be advanced together over second guidewire 274. Once side port 284 is in position, deflection and support catheter 270 can be held in place while first guidewire 272 is advanced out from side port 284 into a branch vessel. Then, second guidewire 274 and deflection catheter 270 can be removed from the patient with first guidewire 272 at its desired position.

Figure 14:
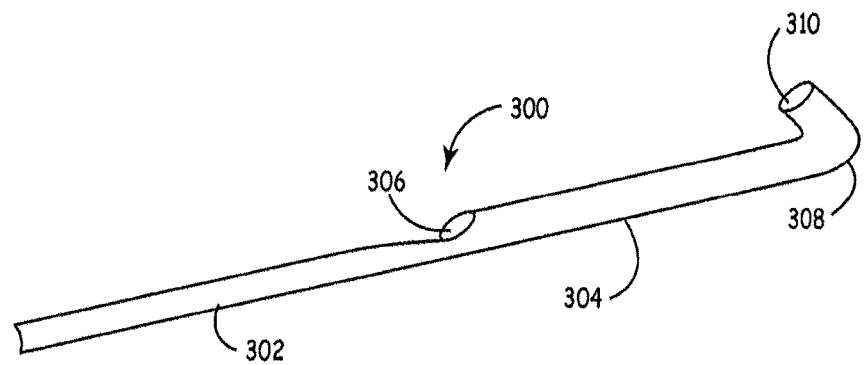
FIG. 14 is a fragmentary perspective side view of a rapid exchange deflection and support catheter having a sharply bent tip.
Figure 15:
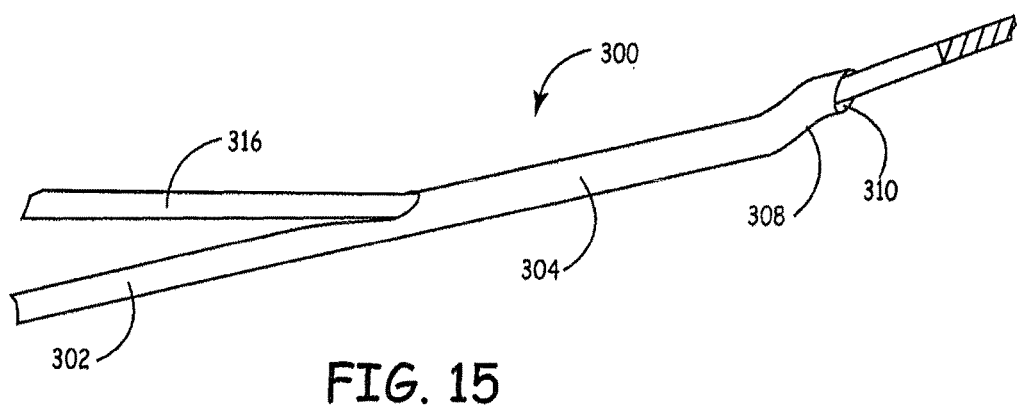
FIG. 15 is a fragmentary side view of the catheter of FIG. 14 engaging an elongated medical device.
Figure 16:
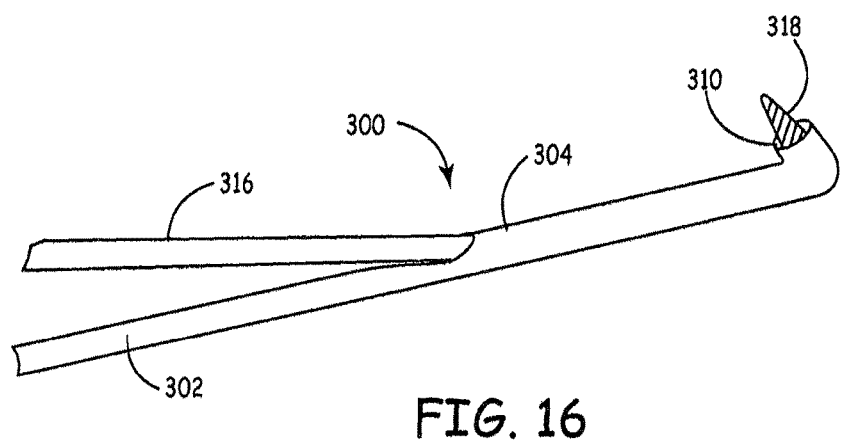
FIG. 16 is a fragmentary side view of the catheter of FIG. 14 engaging an elongated medical device with its tip slightly extending from the bent tip of the deflection and support catheter.

A deflection and support catheter with a distal bent tip is shown in FIG. 14. Referring to FIG. 14, deflection and support catheter 300 has a proximal extension 302, such as a proximal rod, and a rapid exchange segment 304. Rapid exchange segment 304 has a proximal port 306 and a bent tip 308 with a distal port 310. In some embodiments, bent tip 308 in its unstressed position can have an angle of at least about 35 degrees and in some embodiments at least about 45 degrees relative to the natural direction of the remaining portions of rapid exchange segment 304. Referring to FIG. 15, guidewire 316 or other elongated medical device is extending through rapid exchange segment 304 and out from distal port 310. A sufficient length of guidewire 316 extends from distal port 310 so that bent tip 308 flexes to a straighter configuration if any forces tend to hold guidewire 316 in a relatively straight position, such as would be the case in a blood vessel. Referring to FIG. 16, as guidewire 316 is moved in a proximal direction relative to deflection catheter 300, bent tip 308 can resume its natural bent configuration with only guidewire tip 318 extending from distal port 310. If distal port 310 is positioned at a branch vessel, guidewire tip 318 can be advanced into the branch vessel from distal port 310.

Another embodiment of a deflection and support catheter is shown in FIGS. 17 and 18 in which a side port is not used to deflect the medical device. Referring to FIG. 17, deflection and support catheter 330 comprises a proximal extension 332 and rapid exchange segment 334 having a distal port 336 and a proximal port 338. As shown in FIGS. 17 and 18, rapid exchange segment 334 is straight and lacks a side port, although in alternative embodiments, the rapid exchange segment can have a side port that is not used and may be curved. Referring to FIG. 17, rapid exchange segment 334 is riding over medical device 340, which can be a guide wire, microcatheter or other elongated medical device. For deployment, medical device 340 has a sharply bent tip portion 342. As shown in FIG. 18, as deflection and support catheter 330 is advanced near the distal end of medical device 340, rapid exchange segment 334 deflects bent tip portion 342 of medical device 340 to a less bent configuration that provides for placement into a branch vessel.

Figure 19A:
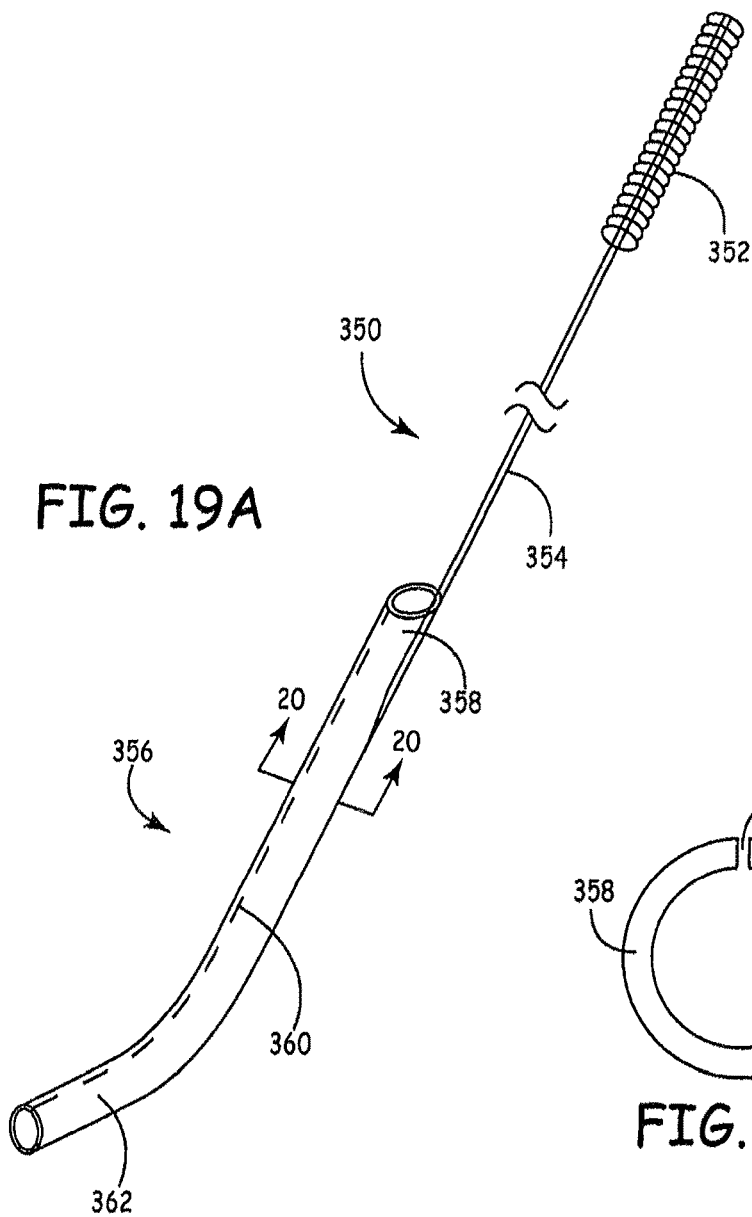
FIG. 19A is a side view of a rapid exchange support catheter.
Figure 20A:
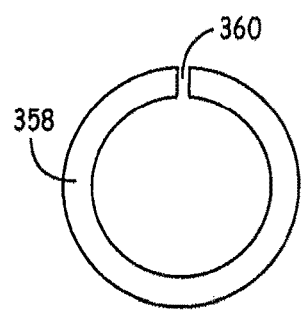
FIG. 20A is a sectional view of an embodiment of the slit rapid exchange segment of the catheter of FIG. 19.
Figure 20B:
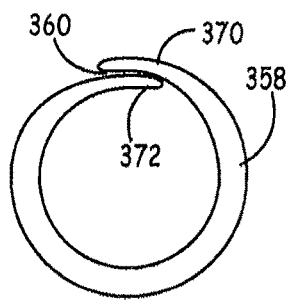
FIG. 20B is a sectional view of an alternative embodiment of the slit rapid exchange segment of the catheter of FIG. 19.
Figure 19B:
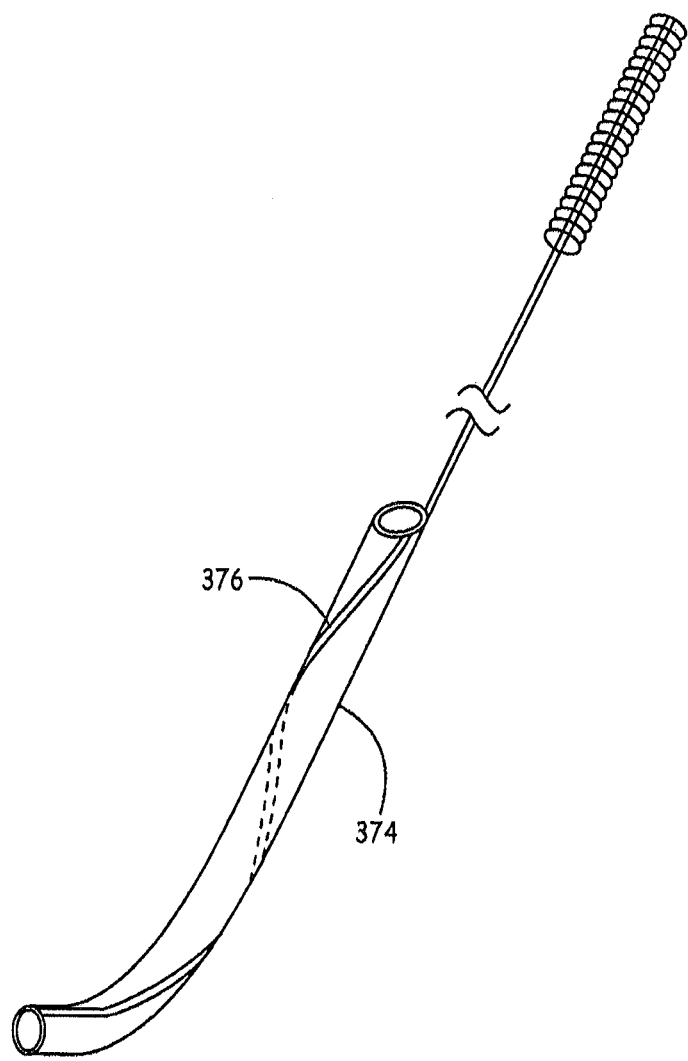
FIG. 19B is a side view of a rapid exchange catheter with a spiral slit.
Figure 19C:
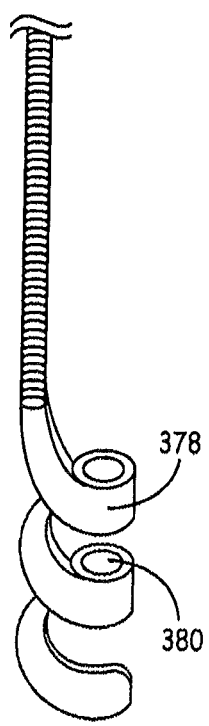
FIG. 19C is a side view of a rapid exchange catheter with a corkscrew slit.
Figure 19D:
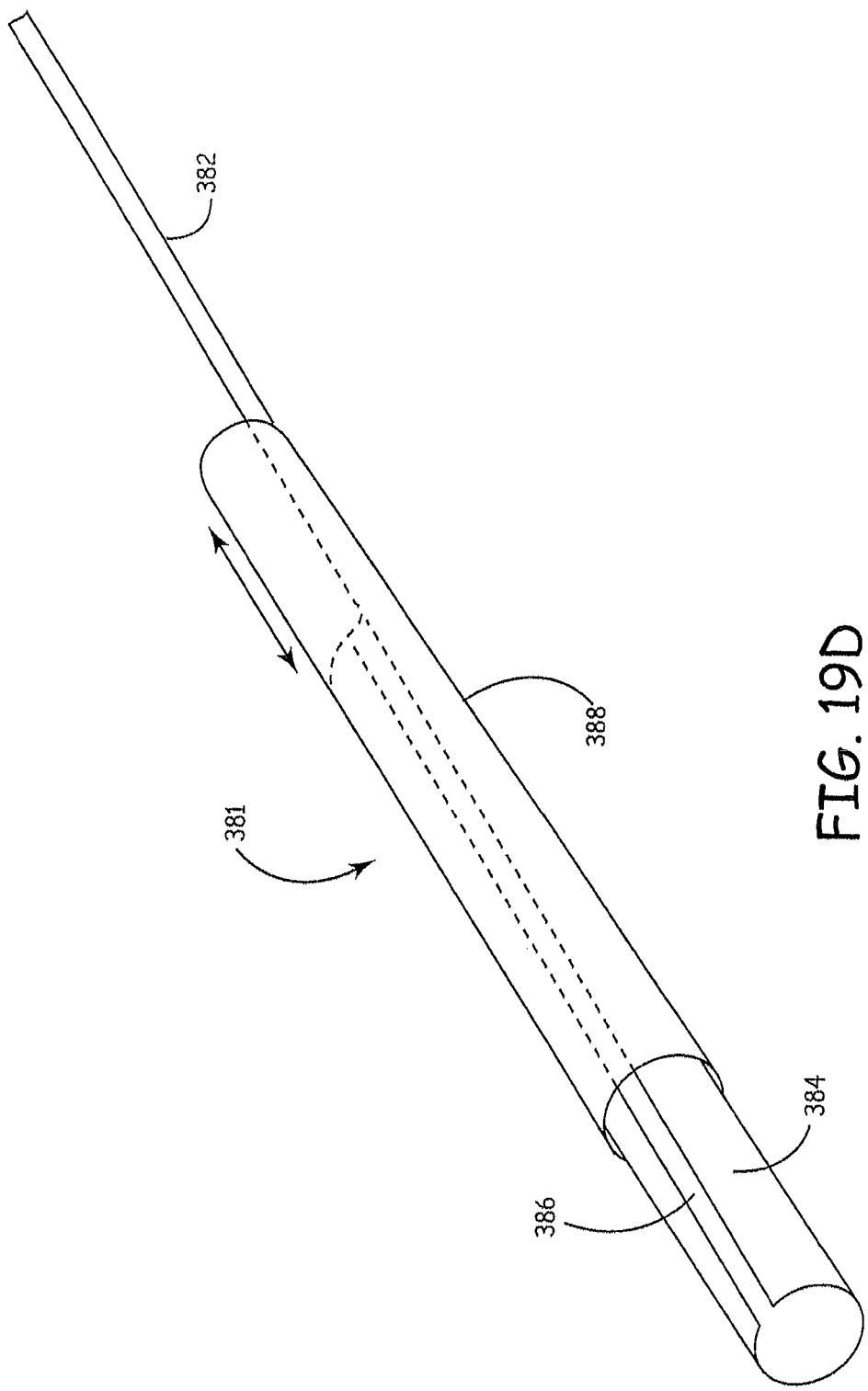
FIG. 19D is a side view of a rapid exchange catheter with an overtube.

An embodiment of a support catheter is shown in FIG. 19A. Support catheter 350 comprises a proximal handle 352, a connecting rod 354 and rapid exchange segment 356 with the connecting rod 354 connecting handle 352 with rapid exchange segment 356. Handle 352 can be formed form any convenient to grip material that is suitable for sterile medical devices. Rapid exchange segment 356 comprises a tubular element 358 with a slit 360 and a gentle curved tip 362. Two suitable, representative cross sections for tubular element 358 with slit 360 are shown in FIGS. 20A and 20B. As shown in FIG. 20A, two blunt edges meet at slit 360. As shown in FIG. 20B, two lips 370, 372 overlap at slit 360. Also, the edges of the slit can interlock, such as with a keyed configuration, for example, as used with a locking plastic sandwich bag, or the like Referring to FIG. 19B, rapid exchange segment 374 has a spiral shaped slit 376 that provides for easy mounting onto a medical device but increased resistance to accidental disengagement. The spiral shaped slit can be exaggerated further to form a cork screw rapid exchange segment, as shown in FIG. 19C. As shown in FIG. 19C, rapid exchange segment 378 has an exaggerated spiral slit 380. Other configurations of the slit structure can be used to provide appropriate ability to expand slit 360 to place rapid exchange segment over a catheter or other elongated medical device while providing after placement over the medical device sufficient rigidity to advance rapid exchange segment 356 over the medical device without any significant chance of disengaging from the medical device inadvertently. Referring to FIG. 19D, support catheter 382 has a proximal push section 382, a rapid exchange section 384 with a slit 386 and an overtube 388. Overtube 388 can be slid off of rapid exchange section 384 for loading and slid over rapid exchange section 384 after loading to restrict disengagement. Friction holds overtube 388 in place after loading.

In one specific embodiment for use in coronary arteries, connecting rod 354 can have a length of roughly 95 centimeters, and rapid exchange segment 356 can have a length of roughly 15 centimeters. Rapid exchange segment can have an inner diameter to fit over a 4 to 4.5 French catheter and an outer diameter to just fit within a 6 F guide catheter. For other applications, a person of ordinary skill in the art can adjust the dimensions of the device appropriately based on the teachings herein.

In general, the deflection/support catheter can be formed from one or more biocompatible materials, including, for example, metals, such as stainless steel or alloys, e.g., Nitinol®, or polymers such as polyether-amide block copolymer (PEBAX®), nylon (polyamides), polyolefins, polytetrafluoroethylene, polyesters, polyurethanes, polycarbonates or other suitable biocompatible polymers. Radiopacity can be achieved with the addition of markers, such as platinum-iridium or platinum-tungsten or through radiopacifiers, such as barium sulfate, bismuth trioxide, bismuth subcarbonate, powdered tungsten, powdered tantalum or the like, added to a polymer resin. Generally, different sections of deflection/aspiration catheter can be formed from different materials from other sections, and sections of the catheter can comprise a plurality of materials at different locations and/or at a particular location. For example, a proximal extended rod/wire can be formed from metal, such as stainless steel. With respect to a rapid exchange segment, one material of particular interest is a themoplastic polymer with embedded metal wire. Suitable polymers include, for example, polyamides, i.e., nylons. The wire can be braided, coiled or otherwise placed over a polymer tubing liner with some tension. A polymer jacket is then placed over the top. Upon heating over the softening temperature of the polymer and subsequent cooling, the wire becomes embedded within the polymer. The liner and jacket can be the same or different materials. Suitable wire for embedding in the polymer includes, for example, flat stainless steel wire. The wire adds additional mechanical strength while maintaining appropriate amounts of flexibility.

The materials generally can be molded, extruded or the like, for example, based on well known processing approaches in the field. Materials can be joined by softening one material and embedding the other material within the softened material, and/or using mechanical reinforcements, clams, brackets or the like. Medical grade materials are generally commercially available for adaptation for forming the structures described herein. Curves can be introduced to polymer material through softening the polymer and hardening the polymer on a curved mandrel or the like.

Use of the Devices

In general, the deflection/support catheters can be used in any reasonable vessels in a patient. However, the deflection/support catheters are particularly useful for directing medical instruments in a patient's blood vessels. In general, the deflection/support catheters are intended to facilitate procedures so that they are easier and faster than difficult procedures using other instruments. Furthermore, the deflection/support catheters are intended to facilitate procedures that otherwise could not be completed since the medical instruments could not be positioned appropriately.

Figures 21, 22:
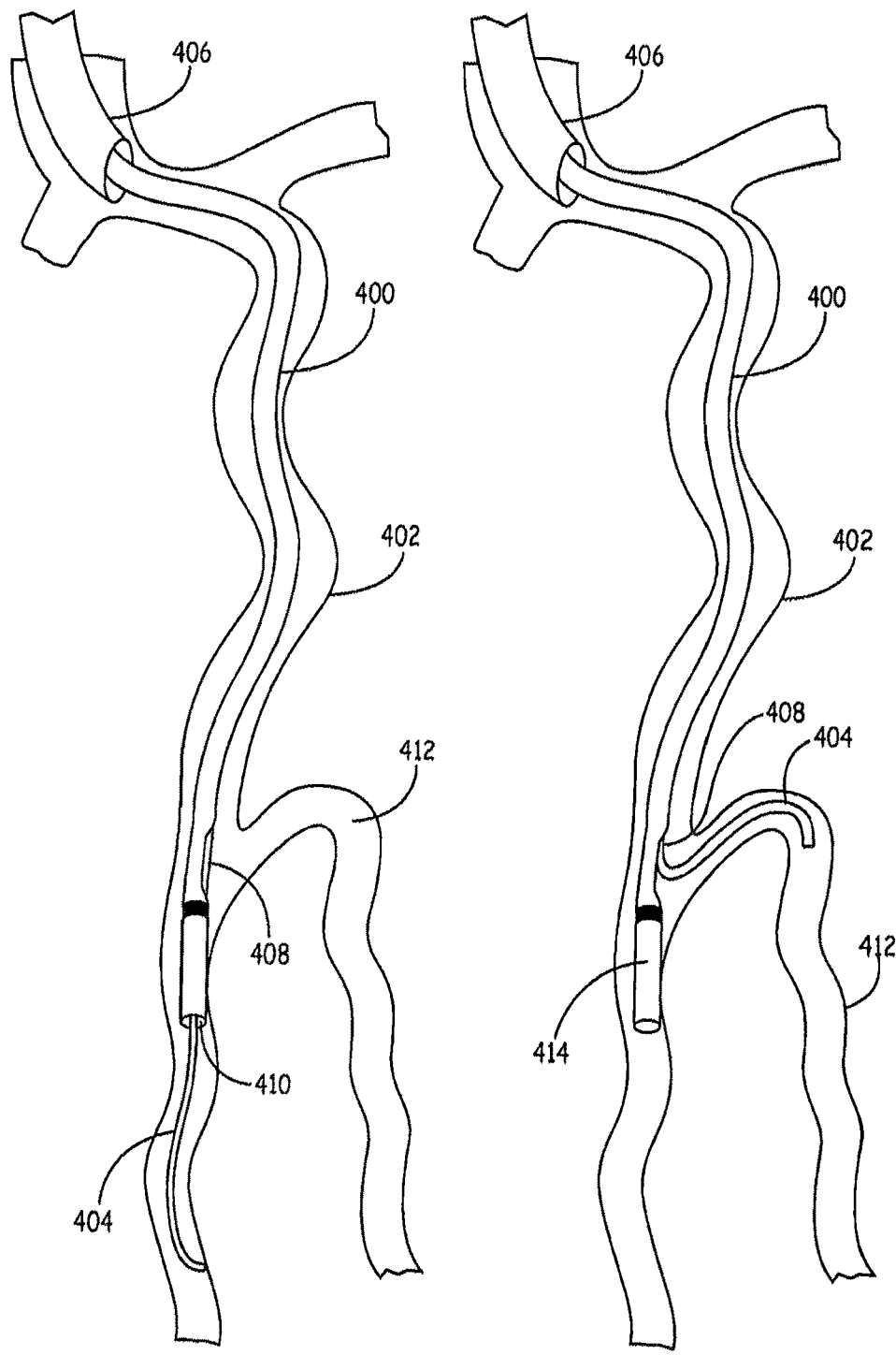
FIG. 21 is a fragmentary schematic view of a deflection catheter riding over a medical device within a blood vessel.
FIG. 22 is a fragmentary schematic view of the deflection catheter in the blood vessels as shown in FIG. 21 with the medical device extending from a side port of the deflection and support catheter.

A general application of a deflection and support catheter is depicted in FIGS. 21 and 22. As shown in FIG. 21, deflection and support catheter 400 has been deployed in a blood vessel 402 over a guidewire 404 or other catheter or elongated medical instrument and through a guide catheter 406. Deflection and support catheter 400 has a side port 408 and a distal port 410. As shown in FIG. 21, guidewire 404 is extending from distal port 410, and side port 408 is positioned near the opening of branch vessel 412.

Referring to FIG. 22, guidewire 404 is shown extending through side port 408 and into branch vessel 412. Distal tip 414 of deflection and support catheter 400 extending distal from side port 408 helps to anchor the deflection and support catheter during the procedure. During the transition from the configuration shown in FIG. 21 to the configuration shown in FIG. 22, guidewire 404 is pulled into distal tip 414 until the tip of guidewire 404 can exit side port 408. Once guidewire 404 has exited side port 408, the guidewire can be advanced into branch vessel 412 with support from deflection and support catheter 400. Once the guidewire is within the branch vessel, the deflection and support catheter can be removed.

Figure 23:
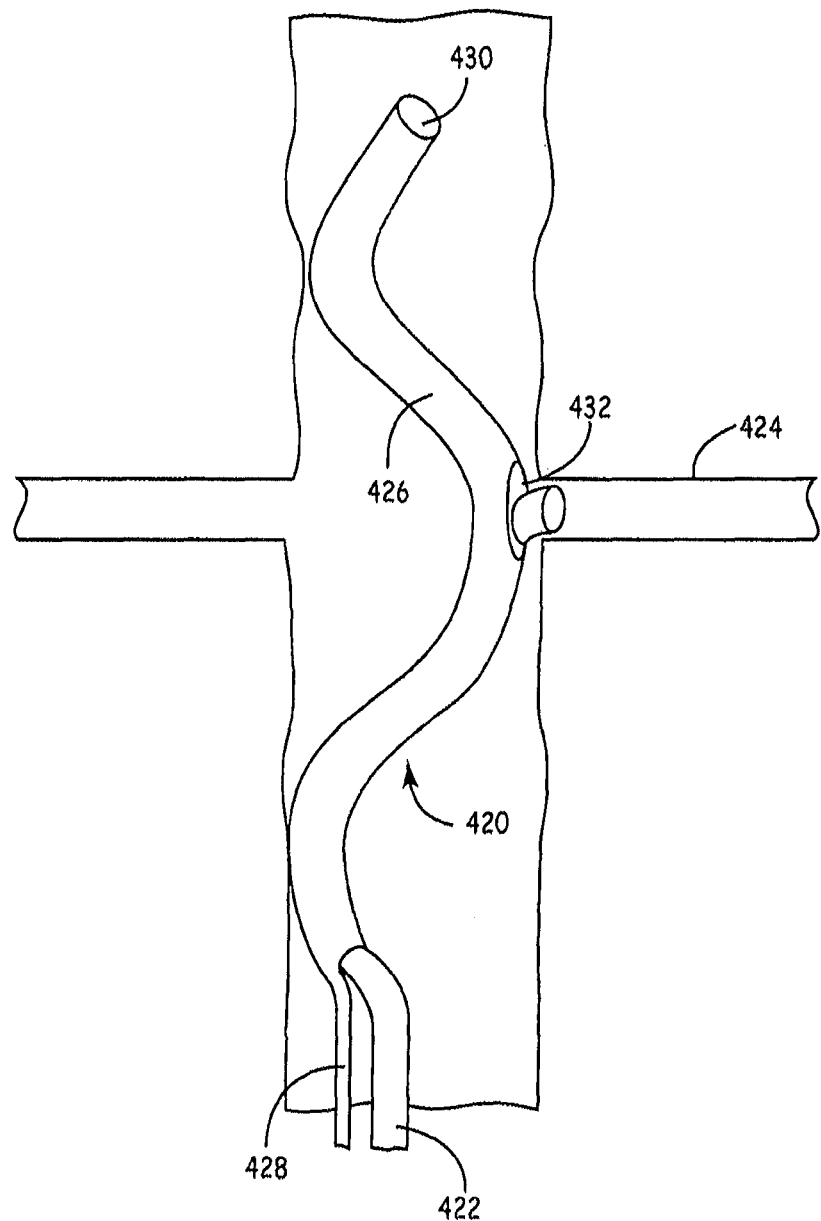
FIG. 23 is a fragmentary schematic view of a deflection and support catheter facilitating deployment of a medical device into a renal artery.

Referring to FIG. 23, a deflection and support catheter 420 is used to deploy a guide catheter 422 into renal artery 424. Deflection and support catheter 420 is shown with a curved rapid exchange segment 426, a proximal flexible rod 428, a distal port 430 and a side port 432. A shown in FIG. 23, the tip of guide catheter 422 is shown exiting side port 432 at the opening into renal artery 424 so that guide catheter 422 can be advanced into renal artery 424 with support form deflection catheter 420.

Figure 24:
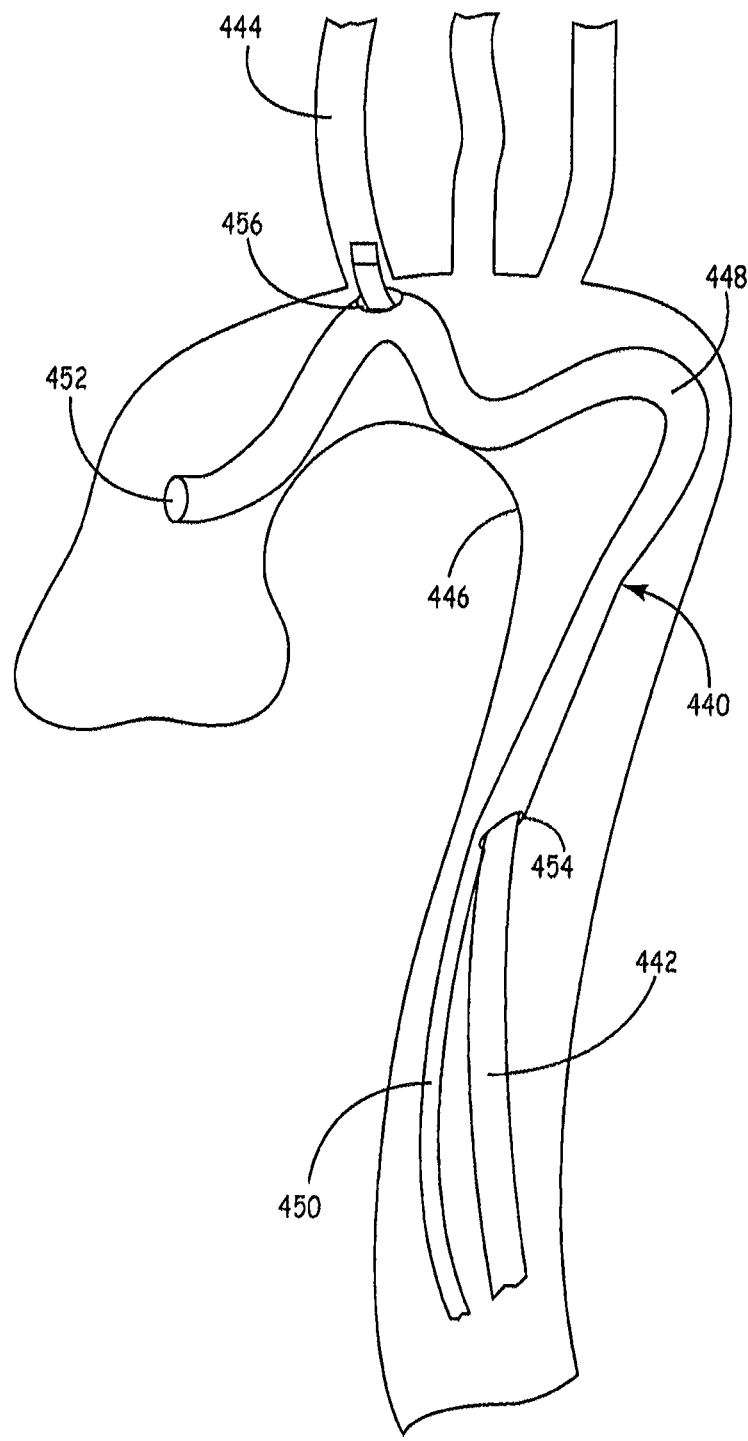
FIG. 24 is a fragmentary schematic view of a deflection and support catheter facilitating deployment of a medical device into a coronary artery.

Referring to FIG. 24, a deflection and support catheter 440 is used to deploy a guide catheter 442 into a coronary artery 444 from aorta 446. Deflection and support catheter 440 is shown with a curved rapid exchange segment 448, a proximal flexible rod 450, a distal port 452, a proximal port 454 and a side port 456. A shown in FIG. 24, the tip of guide catheter 442 is shown exiting side port 456 at the opening into coronary artery 444 so that guide catheter 442 can be advanced into coronary artery 444 with support form deflection/support catheter 440.

Figure 25:
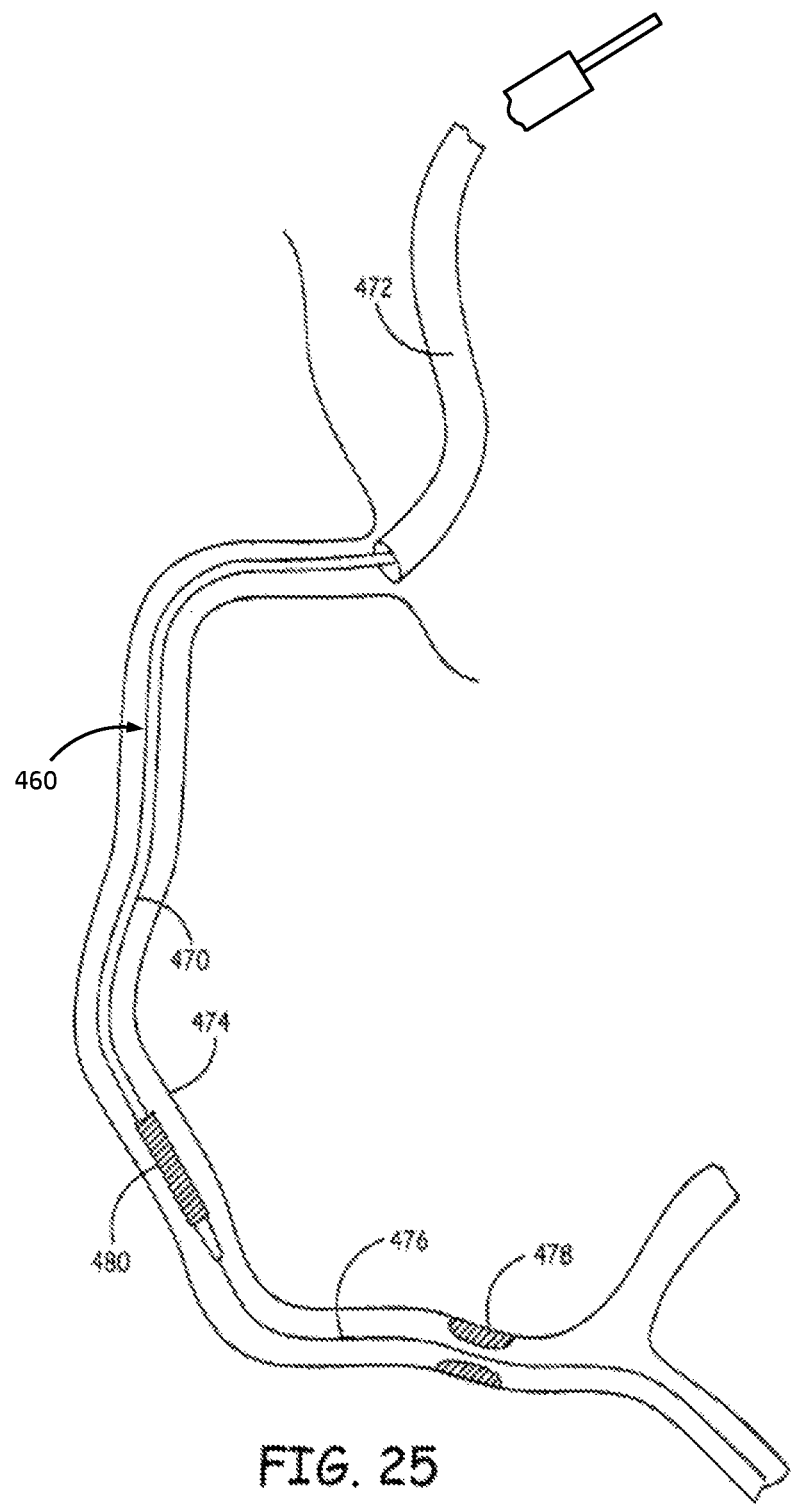
FIG. 25 is a fragmentary schematic view of an elongated treatment structure within a blood vessel proximal to a lesion.
Figure 26:
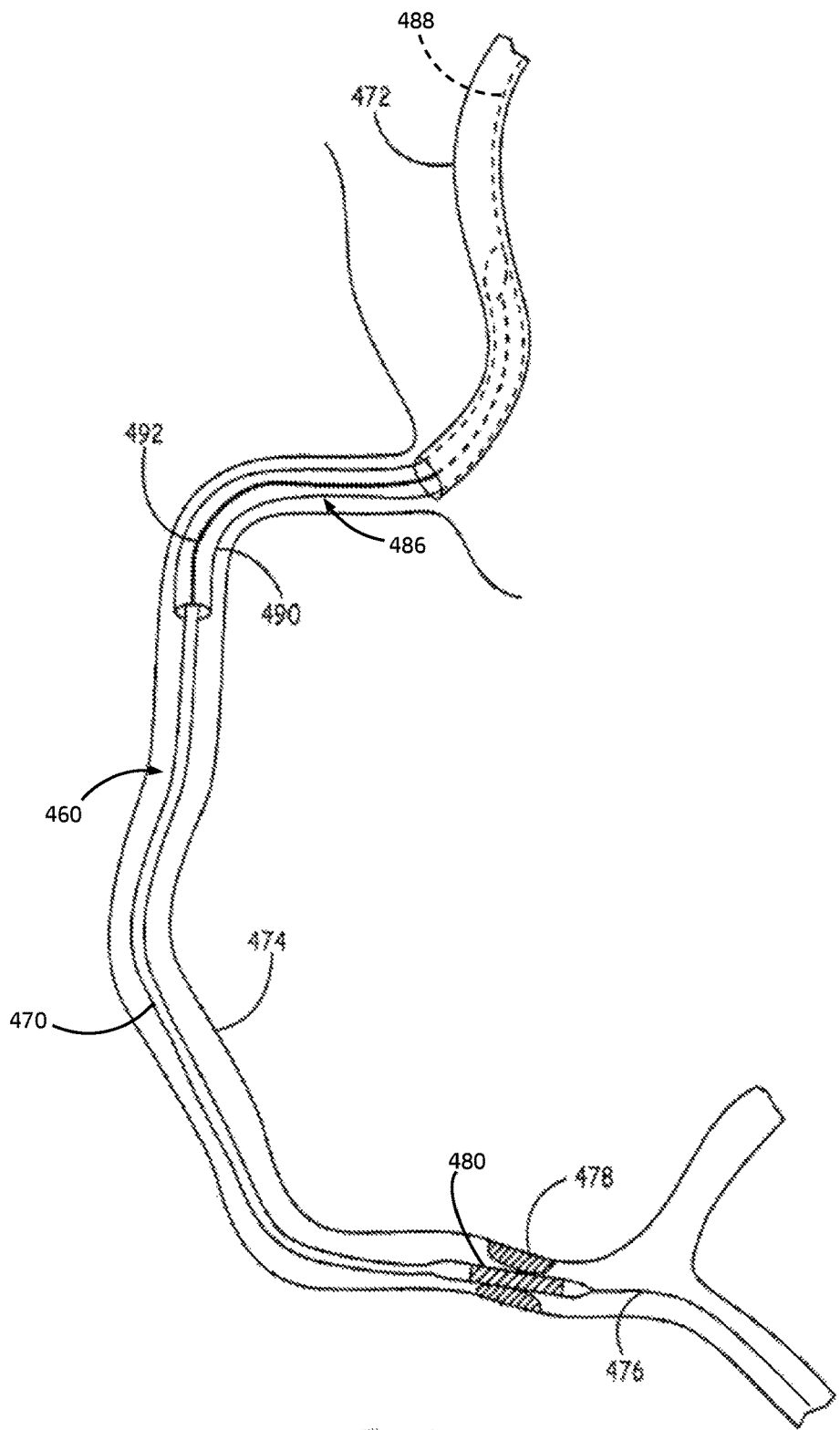
FIG. 26 is a fragmentary schematic view of the treatment structure of FIG. 25 at the lesion following placement facilitated with a support catheter.

The use of a support catheter generally with an elongated medical device 460 is depicted in FIGS. 25 and 26. The elongated medical device 460 includes a treatment catheter 470 carrying a treatment structure 480. Referring to FIG. 25, a distal portion of elongated medical device 460 (e.g., a portion of the treatment catheter 470) extends out from guide catheter 472 into vessel 474 on guidewire 476. Guidewire 476 extends past lesion 478, but it is difficult to advance the treatment structure 480 on treatment catheter 470 to lesion 478 due to the extent of blockage from lesion 478 and the bending of vessel 474. Referring to FIG. 26, support catheter 486 has a proximal segment 488 and a rapid exchange segment including a tubular element 490 and a slit 492 such that the tubular element 490 can be clipped onto a proximal portion of treatment catheter 470. Tubular element 490 is advanced through a Tuohy-Borst valve or the like, through the guide catheter to extend from guide catheter 472 into vessel 474. In some embodiments, tubular element 490 can be extended up to 10 to 12 centimeters into the vessel, such as a coronary artery, graft or the like. With additional support from support catheter 486, treatment structure 480 can be advanced to lesion 478 where a balloon angioplasty, stent deployment and/or other treatment can be performed. Once the lesion is crossed, support catheter 486 can be removed. Suitable angioplasty balloons are described further, for example in U.S. Pat. No. 6,132,824 to Hamlin, entitled "Multilayer Catheter Balloon," incorporated herein by reference. Stent delivery is described further, for example, in U.S. Pat. No. 6,610,069 to Euteneuer et al., entitled "Catheter Support For Stent Delivery," incorporated herein by reference. Various stents and angioplasty balloons are commercially available.

Based on a rough estimate, 10 to 20 percent of procedures have significant difficulty reaching or crossing a lesion with a treatment structure due to proximal vessel tortuosity, calcification and/or the like. The approaches described herein using a support catheter are more generally applicable and are expected to have a greater degree of success relative to approaches based on exchanging devices for a smaller balloon, changing the guide catheter, using a buddy guidewire or the like.

The deflection/support catheters can be sterilized and packaged for distribution using, for example, conventional approaches. Radiation and or chemical sterilization can be used. The packaged catheters can be distributed for use with other medical devices for percutaneous procedures.

The embodiments above are intended to be illustrative and not limiting. Additional embodiments are within the claims. In addition, although the present invention has been described with reference to particular embodiments, those skilled in the art will recognize that changes can be made in form and detail without departing from the spirit and scope of the invention. Any incorporation by reference of documents above is limited such that no subject matter is incorporated that is contrary to the explicit disclosure herein.

What is claimed is:

1. A method for delivering an elongated medical device including a treatment catheter into a vessel within a vascular network, the method comprising:
   (a) positioning the elongated medical device over a guidewire and into a guide catheter, the elongated medical device positioned in the vessel such that a proximal portion of the treatment catheter extends proximally from a proximal end of the guide catheter;
   (b) following step (a), positioning a support catheter comprising a tubular element onto the elongated medical device by urging the proximal portion of the elongated medical device into a lumen defined in the tubular element, the tubular element including a slit structure defined along an entire length of the tubular element;
   wherein throughout step (a) and immediately prior to step (b), the support catheter is not disposed over an entirety of the elongated medical device; and
   (c) advancing the support catheter and the elongated medical device distally through the guide catheter.

2. The method of claim 1, wherein the step of advancing the support catheter and the elongated medical device further comprises urging a proximal segment of the support catheter distally, wherein the proximal segment is coupled to a proximal portion of the tubular element.

3. The method of claim 1, wherein the elongated medical device further includes a treatment structure carried by the treatment catheter, the treatment structure selected from a group consisting of a balloon and a stent delivery structure.

4. The method of claim 1, wherein the step of advancing the support catheter and the elongated medical device further comprises advancing the support catheter such that a distal portion of the tubular element extends from a distal end of the guide catheter into the vessel.

5. The method of claim 4, further comprising advancing the elongated medical device distally to a treatment site in the vessel.

6. The method of claim 1, wherein the slit structure has a spiral configuration.

7. The method of claim 1, further comprising positioning an overtube over the tubular element after positioning the support catheter onto the elongated medical device.

8. The method of claim 1, wherein the slit structure comprises overlapping lips or edges that meet.

9. The method of claim 1, wherein step (a) further includes a distal portion of the elongated medical device extending distally from a distal end of the guide catheter and into the vessel.

10. The method of claim 9, wherein the elongated medical device includes a treatment structure carried by the treatment catheter, and further wherein step (a) further includes the treatment structure located distally beyond the distal end of the guide catheter.

11. The method of claim 1, wherein step (c) includes locating a distal portion of the elongated medical device distally beyond a distal end of the guide catheter, and further wherein following step (c), the method further comprising:
  (d) removing the support catheter while maintaining the distal portion of the elongated medical device distally beyond the distal end of the guide catheter.

12. The method of claim 1, wherein following step (b), the method further comprising distally advancing the tubular element over the elongated medical device.

\* \* \* \* \*